United States Patent [19]

Vicari

[11] Patent Number: 5,628,748

[45] Date of Patent: May 13, 1997

[54] SURGICAL INSTRUMENT

[76] Inventor: Frank A. Vicari, 1303 Hawthorne La., Glenview, Ill. 60025

[21] Appl. No.: 525,255

[22] Filed: Sep. 8, 1995

[51] Int. Cl.$^6$ .................................................. A61B 17/00
[52] U.S. Cl. .......................... 606/79; 606/80; 606/172; 606/176
[58] Field of Search ............................... 606/79, 80, 172, 606/173, 176, 177, 82

[56] References Cited

U.S. PATENT DOCUMENTS

| | | |
|---|---|---|
| 1,748,617 | 2/1930 | Parker . |
| 1,771,764 | 7/1930 | Beattie . |
| 2,176,339 | 10/1939 | Henneman . |
| 2,287,260 | 6/1942 | Luck . |
| 2,367,432 | 1/1945 | Reprogle . |
| 2,429,356 | 10/1947 | Hicks . |
| 3,308,828 | 3/1967 | Pippin . |
| 3,461,875 | 8/1969 | Hall . |
| 3,750,671 | 8/1973 | Hedrick . |
| 4,071,030 | 1/1978 | Hedrick . |
| 4,340,060 | 7/1982 | Berke et al. . |
| 4,625,405 | 12/1986 | Hudnutt et al. . |
| 4,701,128 | 10/1987 | Fitzig et al. ........................ 433/116 |
| 5,304,191 | 4/1994 | Gosselin ........................... 606/172 |

OTHER PUBLICATIONS

Delashaw et al., *Cranial Deformation in Craniosynostosis*, Neurosurgery Clinics of North America, Jul. 1991, vol. 2, No. 3, pp. 611–620.

Green et al., *Treatment of Scaphocephaly with Sagittal Craniectomy and Biparietal Morcellation*, Neurosurgery, 1988, vol. 23, No. 2, pp. 196–202.

Marsh et al., *Surgical Management of Sagittal Synostosis*, Neurosurgery Clinics of North America, Jul 1991, vol. 2, No. 3, pp. 629–640.

McComb, J.G., *Occipital Reduction–Biparietal Widening Technique for Correction of Sagittal Synostosis*, Pediatr Neurosurg 1994;20, pp. 99–105.

Midas Rex Instrumentation Catalog, Fort Worth, Texas, Midas Rex™Pneumatic tools, Inc.

Olds et al., *Surgical Treatment of Sagittal Synostosis*, Neurosurgery 1986, vol. 18, No. 3, pp. 345–347.

Shuper et al., *The Incidence of Isolated Craniosynostosis in the Newborn Infant*, AJDC, Jan. 1985, vol. 139, pp. 85–86.

Sutton et al., *Total Cranial Vault Reconstruction for the Older Child with Scaphocephaly*, Pediatr Neurosurg 1993; 19, pp. 63–72.

*Primary Examiner*—Michael Buiz
*Assistant Examiner*—Mark S. Leonardo
*Attorney, Agent, or Firm*—Leydig, Voit & Mayer

[57] ABSTRACT

A surgical instrument and method are disclosed. The surgical instrument comprises an elongated handle having an operator gripping portion and including a grinding burr rotatably mounted to the handle opposite the operator gripping portion, and an elongated guard connected to the handle and extending along the handle substantially parallel to the axis of the handle, the guard terminating in a plate. The surgical instrument of the present invention allows a surgeon to perform a craniectomy on a patient without reflecting scalp flaps from the skull of the patient.

22 Claims, 6 Drawing Sheets

SURGICAL INSTRUMENT

TECHNICAL FIELD OF THE INVENTION

The present invention pertains to surgical instruments for use in the dissection and cutting of bone and tissue, and to methods pertaining thereto. More specifically, the present invention relates to a surgical instrument for a bone cutting tool including a rotating cutting burr useful in performing cranial surgery on a patient.

BACKGROUND OF THE INVENTION

Surgical instruments with rotating cutting burrs to dissect and cut bone long have been employed in the medical arts. For instance, craniotomes are surgical instruments employed in the surgical procedure known as craniectomy. Craniectomy involves opening the skull so that access may be had to the brain to perform neurosurgery or the like.

Craniotomes often are used in the correction of scaphocephaly. Scaphocephaly, or boat-shaped head, is a cranial dysmorphia that may be immediately apparent at birth, and becomes more difficult to correct with advancing age. This condition is caused by premature craniosynostosis, or fusion of the cranial sutures, specifically, the saggital suture. Although neurological signs and symptoms have been reported in untreated cases, the only clear indication for surgical correction of scaphocephaly is cosmesis. If not treated, children with scaphocephaly can be the subject of unpleasant discrimination by peers and may have significant psychosocial problems. Surgical correction should be recommended for most, if not all, children who have this cranial dysmorphia.

Many treatments for scaphocephaly have been proposed. See, e.g. Greene, Jr., et al., "Treatment of Scaphocephaly with Sagittal Craniectomy and Biparietal Morcellation," *Neurosurgery* 23:2, 196–202 (1988); Olds, "Surgical Treatment of Sagittal Synostosis," *Neurosurgery* 18:3, 345–347 (1986); Sutton et al., "Total Cranial Vault Reconstruction for the Older Child with Scaphocephaly," *Pediatr. Neurosurg.* 1993:19, 63–72 (1993); McComb, "Occipital Reduction-Biparietal Widening Technique for Correction of Sagittal Synostosis," *Pediatr. Neurosurg.* 1994:20 99–106 (1994); Marsh et al., "Surgical Management of Sagittal Synostosis," *Neurosurgery Clinics of North America* 2:3, 629–640 (1991). In the simplest of these treatments, a strip at the center of the skull is surgically removed, thereby allowing the skull to expand under pressure of the expanding brain. For example, wide sagittal craniectomy with or without biparietal outfracture is a preferred procedure when the patient is very young (under age six months). In such infants, the pressure of the expanding brain causes the skull to reshape itself. The cranial bone ultimately grows back and fuses to thereby reform the complete skull.

When the patient reaches an older age, such as about nine to twelve months, craniectomies become much more difficult to perform. The brain no longer expands at a rate sufficient to reshape the skull, and the skull itself has thickened to such an extent that it may not remodel significantly. Moreover, the skull may not reossify after surgery, thus requiring reconstruction of the skull. F o r such patients, more radical procedures must be used to force the skull to reshape itself. For example, in the subtotal craniectomy procedure, a portion of the skull is removed and physically reshaped by the surgeon, then replaced.

All of the foregoing procedures generally are accomplished by means of a conventional surgical drill, which typically includes a handle and a cutting means for cutting the skull of a patient. The dura mater, or dura, is a tough membrane that surrounds the brain in mammals. Generally, a surgeon should not pierce this dura in operations to correct scaphocephaly. Accordingly, conventional surgical instruments include a guard for preventing the cutting means from piercing the dura of the patient.

In performing an operation using such previously available drills, the scalp of the patient is completely reflected from the skull. This process entails incising the scalp near the center and pulling the scalp flaps to either side or front and back, thus completely exposing the skull. An incision is made in the skull, and the surgical drill is then used to remove portions of the skull.

Use of such a conventional surgical drill suffers from a number of drawbacks, however, which the present invention seeks to overcome. These disadvantages stem from the aforementioned need to completely reflect the scalp from the skull of the patient. For instance, upon conclusion of the craniectomy when the scalp flaps have been reflected, the scalp must be sewn shut. This may cause scarring and creates additional risk of infection. In addition, increased surgical time is required to open and close longer incisions. Increased blood loss and post operative swelling, resulting in longer hospital stays, are further disadvantages.

In addition, many surgeons are reluctant to reflect the scalp from very young infants, such as age four months. Surgical correction of scaphocephaly is preferred at as early an age as is surgically permissible, inasmuch as the brain most rapidly expands during the earliest months. If a surgeon is reluctant to perform a craniectomy on a patient because of the need to reflect the scalp, this reluctance may prevent the surgeon from performing a craniectomy until the patient has reached an age of several months. The patient may then require a more radical surgical procedure than that previously required.

A prior art surgical instrument is shown in FIG. 1. Such instruments are available, for example, from MIDAS REX® PNEUMATIC TOOLS, INC., Fort Worth, Tex. The instrument 20 comprises a handle 21 including a side-biting burr 22. The tip 23 of the burr 22 is protected by a guard 24 having a laterally extending foot 25, which prevents the tip 23 from piercing the dura of a patient. The burr 22 is powered by a drive shaft extending through an axial bore in the handle 21. The drive shaft is driven by a motor, which is coupled to the operator gripping portion 26 and which typically is driven by a source of compressed air. Such prior art device is exemplified by the device disclosed in U.S. Pat. No. 5,304,191, assigned to MIDAS REX® PNEUMATIC TOOLS, INC. Because the side-biting burr extends from the handle at a direction generally coaxial with the axis of the handle, the surgeon cannot access the scalp without reflecting scalp flaps from the patient.

To avoid these shortcomings, it is a general object of the present invention to provide a surgical instrument useful in the performance of cranial surgery that avoids the need to reflect the scalp from the skull of the patient. Another object is to provide a guard for a surgical saw which deflects and protects the dura during cranial surgery without the need to reflect the scalp. A further object of the present invention is to provide a method for cranial surgery, which method avoids the need to reflect the scalp.

BRIEF SUMMARY OF THE INVENTION

The present invention overcomes the drawbacks inherent in prior art surgical devices by providing a surgical instrument comprising, in one embodiment, an elongated handle having an operator gripping portion and including a grinding burr, or saw, rotatably mounted to the handle opposite the operator gripping portion and extending in a direction generally perpendicular to the axis of the handle. An elongated guard is connected to the handle and extends along the handle substantially parallel to the axis of the handle. The guard preferably terminates in a broadened distal end extending just past the burr.

The present surgical instrument is adapted to fit under the scalp of the patient. When using the surgical instrument according to the invention, the surgeon need only make a small incision in the scalp. The surgical instrument then may be inserted under the scalp to remove cranial bone, and the scalp need not be reflected at all. When the operation is complete, only the small scalp incision must be sewn shut, rather than two complete halves of reflected scalp.

A method of extracting cranial bone in a mammal also falls within the scope of the present invention. The method comprises the steps of incising the scalp of the mammal, gripping a surgical instrument according to the present invention, incising the skull of the mammal, positioning the surgical instrument in a position wherein the handle is below the scalp of the mammal but above the skull of the mammal and wherein the guard is below the skull of the mammal but above the dura of the mammal; and cutting the skull of the mammal with the burr to thereby remove the cranial bone. The method of the present invention preferably avoids the need to reflect scalp flaps.

A guard for a surgical instrument also falls within the purview of the present invention. The guard comprises a shaft having a proximal end and a broadened distal end, the broadened distal end extending in a direction generally collinear with the axis of the shaft.

Further, the present invention encompasses a method of cranial surgery in a mammal. The method comprises the steps of providing an endoscope, the endoscope including a proximal end grippable by a user and a distal end including visual transmission means, positioning the endoscope between the inner table of the skull of the mammal and the dura of the mammal, and separating the dura from the skull using the endoscope for direct visualization.

DESCRIPTION OF THE PREFERRED EMBODIMENTS

Figure 1:
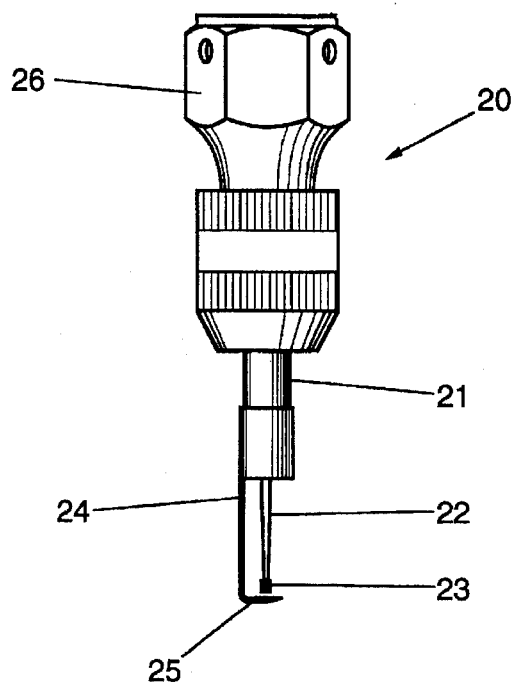
FIG. 1 is a perspective view of a prior art craniotome.
Figure 2:
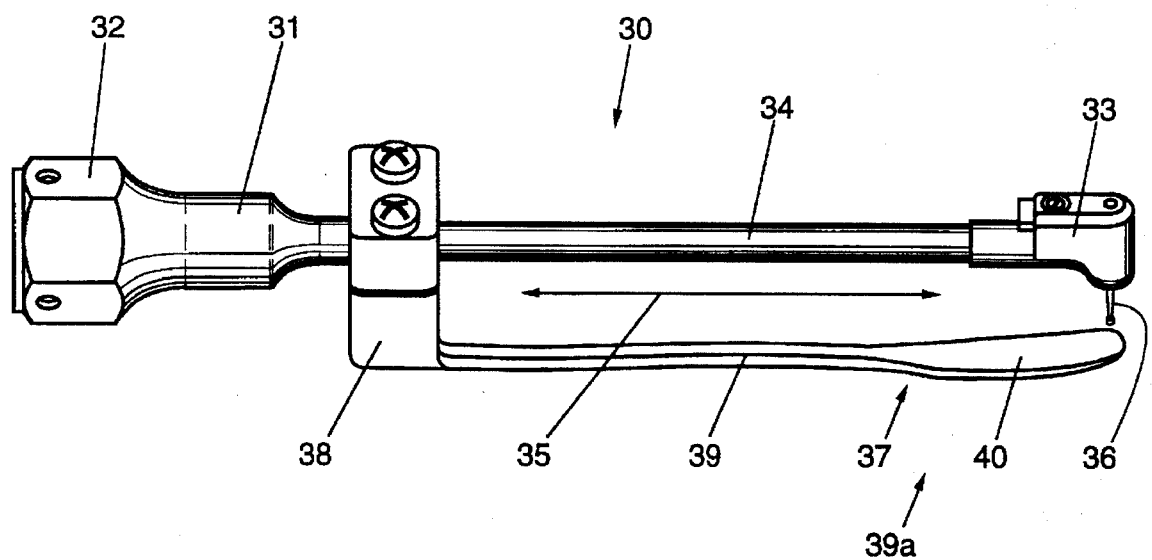
FIG. 2 is a perspective view of a surgical instrument according to the present invention having a side-biting burr and a guard.
Figure 3:
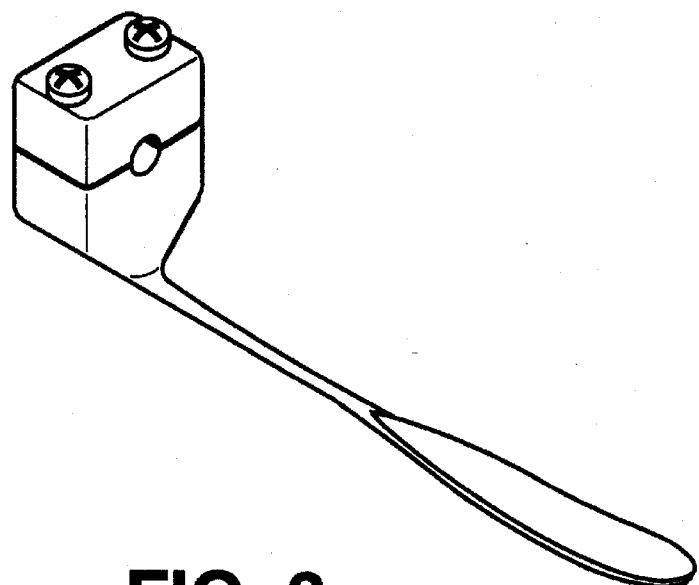
FIG. 3 is a perspective view of a guard for a surgical instrument according to the present invention.

FIGS. 2–8 and 11 illustrate a surgical instrument and guard according to the present invention. The instrument 30 comprises a handle 31 connecting an operator gripping portion 32 to a cutting head 33 via a shaft 34. Extending from the cutting head 33 in a direction generally perpendicular to the axis 35 of the handle 31 is a side-biting burr 36. The handle 31 preferably is cylindrical in cross section, at least at the shaft 34, although other suitable shapes may be used. For example, the handle may have a square cross-section.

The shaft 34 preferably includes an axial bore through which passes a drive shaft or comparable means for driving the side-biting burr. Handle 31 may include a coupling for linkage to a conventionally available motor M, shown schematically in FIG. 7. The motor M preferably is driven by source of compressed gas, but may instead be driven by other suitable means, such as electrically. Such suitable motors and couplings are widely known in the art. In the preferred embodiment, the cutting head 33 includes a bevel gear assembly for converting the rotation of the drive shaft to the 90° rotation of the side-biting burr 36. The surgeon thus is able to actuate the burr 36 when desired by actuating the motor coupled to the handle 31.

Figure 4:
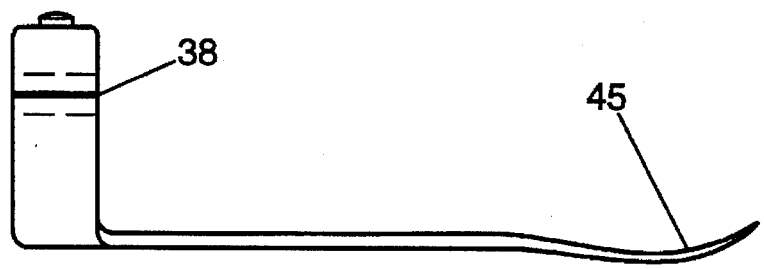
FIG. 4 is a side elevational view of the guard illustrated in FIG. 3.

The surgical instrument 30 includes a guard 37 secured to the surgical instrument 30. The guard 37 preferably is releasably secured to the handle 21 at the shaft 34. The guard 37 may be attached to the surgical instrument 30 in any suitable manner. The guard 37 should be cantilevered to the shaft 34. Preferably, the guard 37 comprises a collar 38 and a rigid stem 39 extending from the collar 38 in a direction generally parallel to the axis 35 of the handle. The guard 32 preferably is parallel to the handle along the length of the guard, although the guard may be cantilevered such that it extends from the shaft 34 at an angle. The guard 32 should not be parallel to the burr 36, but should be approximately perpendicular thereto. The stem 39 terminates at its distal end 39a in a plate, or broad portion 40, proximal the tip of the burr 36 and spaced apart with respect thereto. The guard 37 prevents the burr 36 from penetrating the dura. Preferably, the broad portion 40 itself terminates in an upturned tip as best illustrated in FIG. 4. The upturned tip 45 assists the broad portion 40 in separating dura from the skull of a patient, and prevents the burr 22 from penetrating dura as it moves transversely across the skull of the patient in the process of cutting bone.

The guard 37 should be suitably dimensioned so that the side-biting burr may cut the skull of the patient, whether a human infant or an adult, when the cutting head 33 is beneath the scalp of the human patient and when the guard 37 is beneath the skull but above the dura of the human patient. In the preferred embodiment of the present invention, the broad portion 40 extends in a direction generally parallel to that of the axis 39 of the handle 31.

Figure 5:
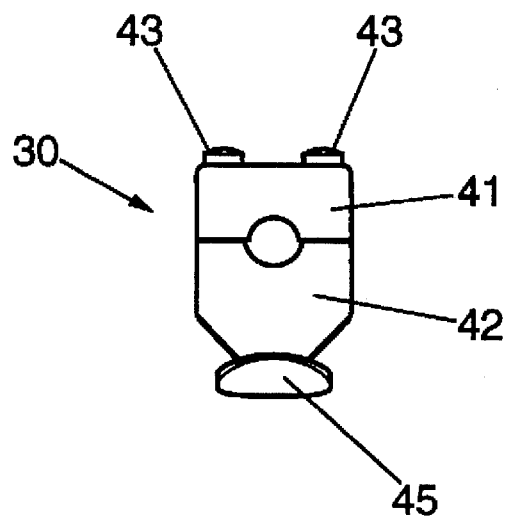
FIG. 5 is a front elevational of the guard illustrated in FIG. 3.
Figure 6:
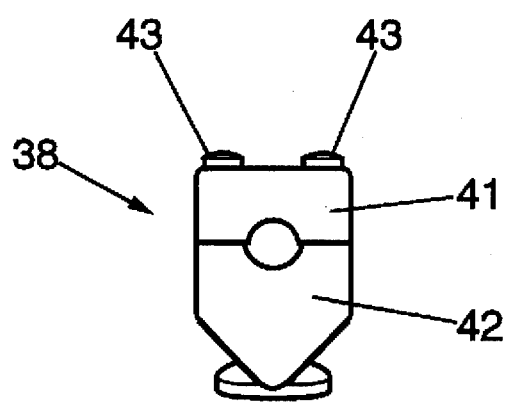
FIG. 6 is a rear elevational view of the guard illustrated in FIG. 3.
Figure 7:
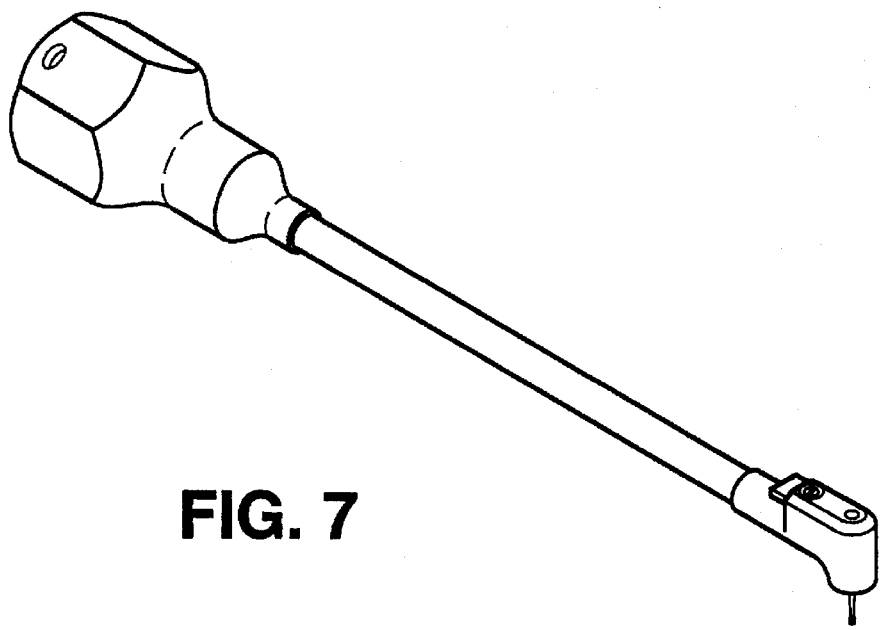
FIG. 7 is a perspective view of the handle of a surgical instrument according to the present invention, including a side-biting burr.
Figure 8:
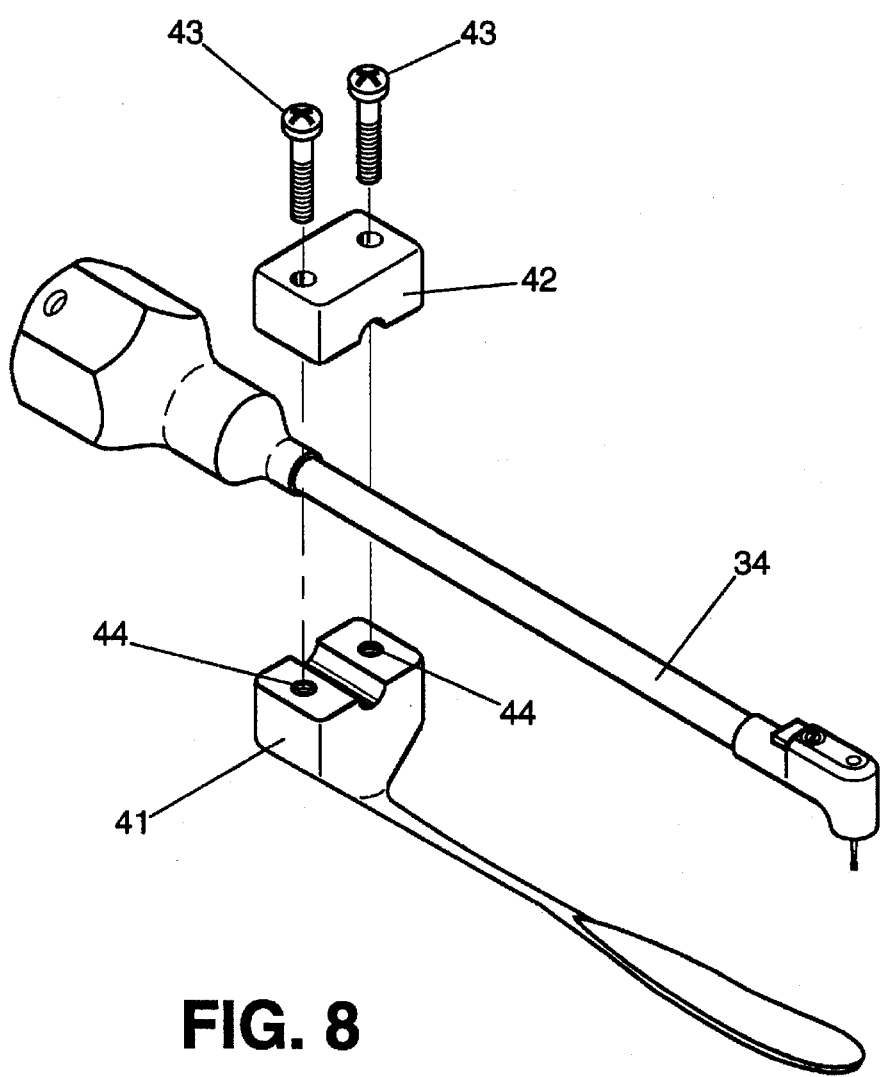
FIG. 8 is an exploded view of a surgical instrument according to the present invention as seen in FIG. 2.

FIGS. 5–8 further illustrate the preferred means of connecting the guard 37 to the surgical instrument 30, As shown in FIGS. 5 and 6, a collar 38 is provided. The collar 38 comprises upper and lower collar members 42, 41, each containing a groove in the approximate shape of a semicircle to thereby form a bore when the upper and lower collar members are joined. As shown in FIG. 8, the collar connects to the shaft 34 by means of fastening screws 43, which seat in threaded sockets 44 in the lower collar member 41. The guard may be adjustable to vary the distance between the broad portion 40 and the tip of the burr 22, for example, by means of spacers between upper and lower collar members 42, 41.

Preferably, the upper collar member 42 is not perfectly semicircular in cross section, but rather is truncated such that when the upper collar member 42 and the lower collar member 42 are mated a keyhole-shaped bore results rather than a perfectly circular bore. FIGS. 5 and 6 best illustrate the keyhole-shaped cross section of the bore. Accordingly, the passage in the collar 38 receiving the shaft 34 is slightly eccentric, thus allowing the collar 38 to securely grip the shaft 34. Preferably, the collar is so made by drilling the passage in the collar prior to separating the upper and lower collar members. A portion of the lower surface of the upper collar member is then removed, thereby truncating the semicircular groove in the upper collar member.

By means of the collar, the guard 37 is movably mounted to the handle 31. Preferably, the guard 37 is slideably mounted to the handle 31. Thus, the broad portion 40 may be positionable with respect to the side-biting burr 36 and may be used with handles of various length.

The surgical instrument preferably is made of stainless steel, but may be made out of any surgically acceptable material. The side-biting burr may be any suitable commercially available burr, such as one sold by MIDAS REX® PNEUMATIC TOOLS, INC. under the tradename MIDAS REX DISSECTING TOOL AF-4.

Figure 9:
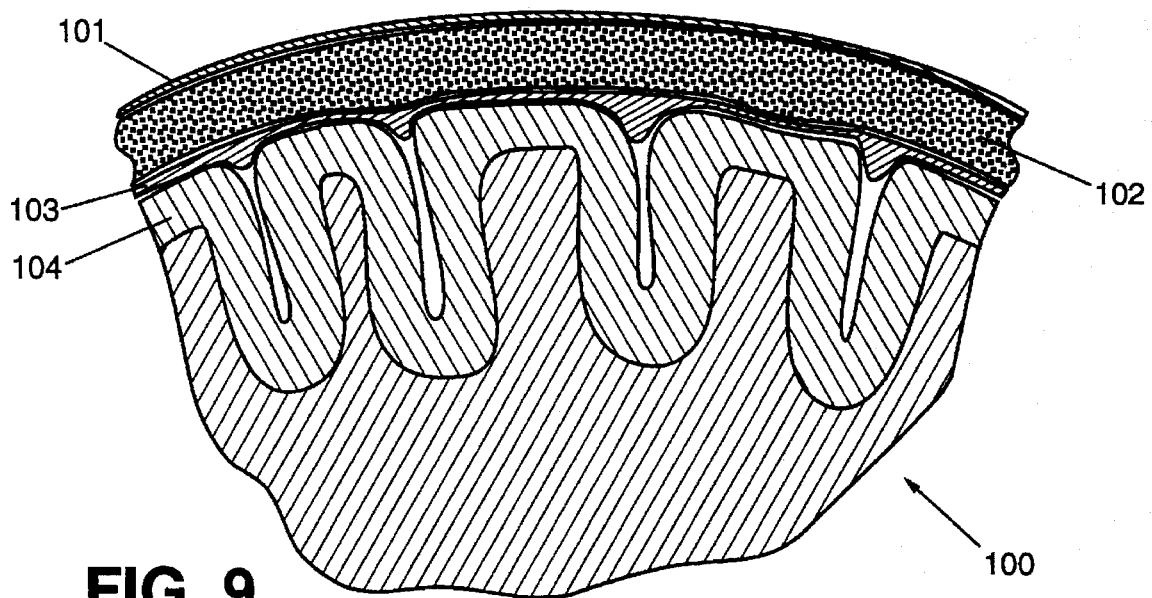
FIG. 9 is a cross sectional view of the head of a patient showing the skull, dura and brain matter.
Figure 10:
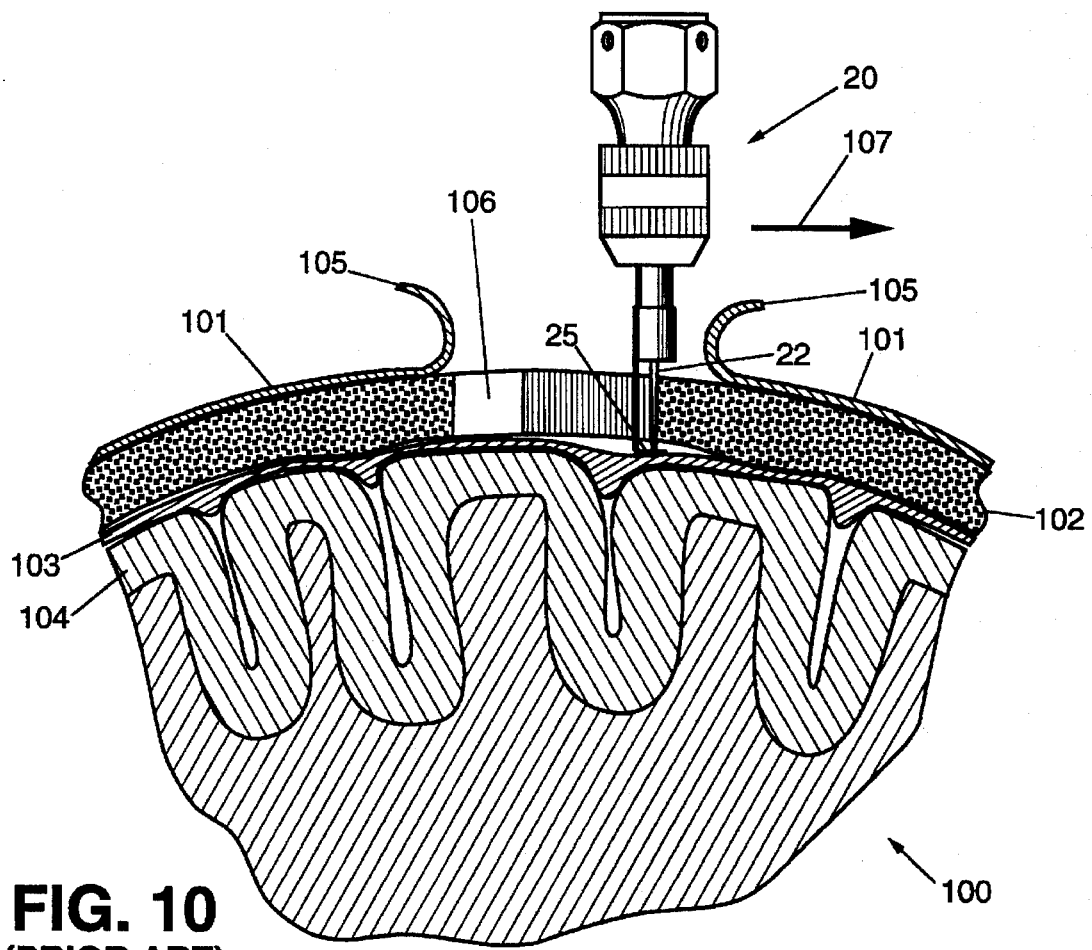
FIG. 10 is a side view of the prior art instrument illustrated in FIG. 1 as it is used to perform a craniectomy on a surgical patient.
Figure 11:
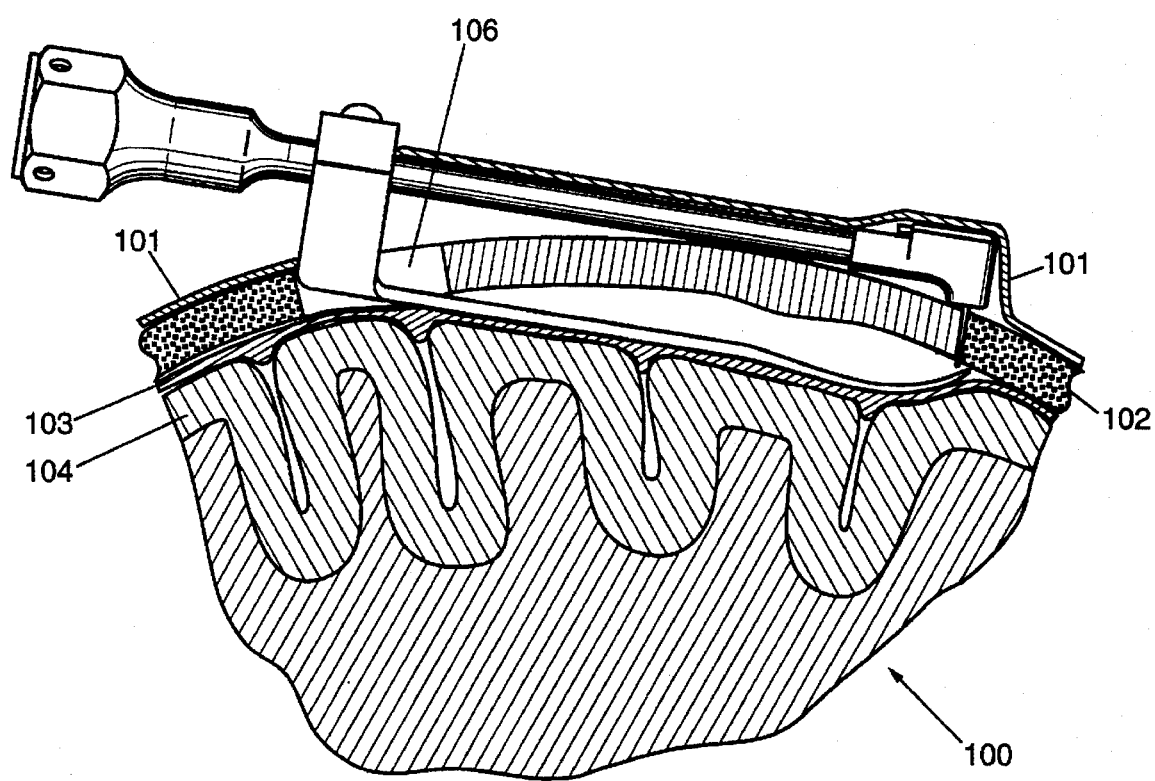
FIG. 11 is a side view of a surgical instrument of the present invention illustrated in FIG. 2, illustrating the performance of a craniectomy on a surgical patient.

Operation of the surgical instrument is illustrated in FIGS. 9–11, where like numerals designate like parts. FIG. 9 illustrates the head 100 of a human patient. The head 100 comprises scalp 101, skull 102, dura 103, and brain 104.

FIG. 10 illustrates a surgical procedure performed using a prior art surgical drill such as that illustrated in FIG. 1. Prior to cutting the skull 102, the surgeon incises the scalp 101 and reflects scalp flaps 105. After an initial bore 106 is made in the skull 102, the surgical instrument 20 is lowered until the foot 25 reaches the dura 103. The burr 22 then cuts transversely across the skull 102 in the direction of arrow 107 to thereby remove portions of bone from the skull 102. The foot 25 separates the dura 103 from the skull 102 and prevents the burr 22 from penetrating into the brain 104. This procedure may not be accomplished without reflecting scalp flaps along almost the entire portion of the skull where bone will be removed.

FIG. 11 illustrates a surgical operation using the surgical instrument of the present invention. A small incision is made in the scalp 101, and a bore 106 is made in the skull 102. The scalp 101 need not be reflected. The surgical instrument then is inserted into the bore in a position wherein the handle 31 is below the scalp 101 but above the skull 102 and wherein the guard 37 is below the skull 102 but above the dura 103. The side-biting burr 36 then is actuated and is used to cut away portions of the skull 102. The particular surgical procedure employed will be chosen at the discretion of the surgeon.

In a preferred embodiment of the present invention, the surgery is endoscopically assisted. A conventional endoscope, such as that manufactured by SNOWDEN-PENCER, may be used. The endoscope transmits an image from its distal end to its proximal end, where the image is enlarged and viewed by the surgeon. Use of the endoscope allows the surgeon to view the progress of the surgical dissection, separating the dura from the skull 102 of the patient. In a particularly preferred embodiment, the endoscope is inserted between the dura 103 and the skull 102 prior to use of the surgical instrument. The distal end of the endoscope then is used to visualize the dura 103. A dissection device, such as a suction device, then is used to continue to dissect dura away from the skull 102. This further minimizes the risk that the burr 36 will penetrate the dura 103, and allows the dura 103 to be deflected under direct vision, i.e., endoscopically viewed.

In performing bone excision using the surgical instrument of the present invention, two small incisions are made in the scalp, one over the area of the anterior fontanelle and one posteriorly over the lambdoid suture. By using two such small incisions, visual control of the surgical instrument over the sagittal sinus may be maintained. An endoscope may be inserted into either scalp incision to assist in maintaining visual control. Two posterior burr holes are drilled, one on either side of the sagittal sinus. The surgical instrument of the present invention then is used to cut across the sagittal suture.

The dura 103 next is dissected away from the inner table of the skull under those portions of the skull to be removed. Preferably, this step is performed using an endoscope, wherein the dura 103 is dissected from the skull 102. The surgical instrument then is inserted into the burr holes such that the guard is below the skull 102 of the patient but above the dura 103. Bone is then cut from the skull by the surgeon and removed through the scalp incisions.

After performing the craniectomy, the parietal plates are severed by osteotomy along the area of the lambdoid and coronal sutures. The surgical instrument and endoscope then are removed, and the scalp incisions then are closed, using the surgeon's suture of choice. Drains may be used if the surgeon desires.

The present invention enhances the safety and efficacy of cranial surgery. Scalp flaps need not be reflected; thus, scarring, potential infection sites, and other drawbacks of conventional surgical procedures are minimized. The present invention thus overcomes the drawbacks inherent in prior surgical instruments and methods.

While particular embodiments of the invention have been shown, it will of course be understood that the invention is not limited thereto since modifications may be made by those skilled in the art, particularly in light of the foregoing teachings. For example, the method of the present invention may be employed in the correction of coronal synostosis, of metopic synostosis, or of pansynostosis, with cranial reshaping performed as necessary. The instrument has utility in conventional cranial surgical methods, wherein scalp flaps are reflected. Indeed, the surgical instrument of the present invention has applications other than cranial surgery, for example, in removing casts from a limb of patient. It is, therefore, contemplated by the appended claims to cover any such modifications as incorporate those features which constitute the essential features of these improvements within the true spirit and scope of the invention. All references cited herein are hereby incorporated by reference in their entireties.

What is claimed is:

1. A surgical instrument for cutting cranial and/or facial bone from a mammal, said mammal having cranial bone at least partially covering a brain, said mammal having a dura substantially separating said brain from said cranial bone, said mammal having a scalp covering at least a portion of said cranial bone, the surgical instrument comprising:

an elongated handle having an operator gripping portion, said handle having an axis, said handle including a grinding burr rotatably mounted to said handle opposite said operator gripping portion and extending therefrom in a direction generally perpendicular to the axis of said handle; and an elongated guard connected to said handle, said guard extending along said handle substantially parallel to the axis of said handle, said guard terminating in a plate, wherein said surgical instrument is adjustable to an operating position wherein said grinding burr is below said scalp but above said skull of said mammal and wherein said guard is below said skull of said mammal but above said dura of said mammal.

2. A surgical instrument according to claim 1, wherein substantially the entire length of said guard is substantially perpendicular to the axis of rotation of said grinding burr.

3. A surgical instrument according to claim 1, wherein said burr is a side-biting burr.

4. A surgical instrument according to claim 1, said grinding burr rotatable about an axis generally perpendicular to the axis of said handle.

5. A surgical instrument according to claim 1, wherein said guard is connected to a collar, wherein said collar releasably secures said guard to said handle.

6. A surgical instrument according to claim 5, wherein said collar is movable along said handle.

7. A surgical instrument according to claim 5, said collar including at least one screw for releasably securing said collar to said handle.

8. A surgical instrument according to claim 1, wherein said handle is substantially cylindrical along at least a portion of its length.

9. A surgical instrument according to claim 1, said surgical instrument including a drive shaft extending through an axial bore in said handle, said burr driven by said drive shaft.

10. A surgical instrument according to claim 9, said drive shaft driven by a motor coupled to said handle, said motor driven by source of compressed air.

11. A surgical instrument according to claim 1, wherein said guard plate includes an upturned tip.

12. A method of extracting cranial bone from a mammal, said mammal having cranial bone at least partially covering a brain, said mammal having a dura substantially separating said brain from said cranial bone, said mammal having a scalp covering at least a portion of said cranial bone, said method comprising the steps of:

incising the scalp of said mammal;

gripping a surgical instrument, said surgical instrument comprising:

an elongated handle having an operator gripping portion, said handle having an axis;

a grinding burr mounted to said handle opposite said operator gripping portion and rotatable about an axis generally perpendicular to the axis of said handle and extending therefrom in a direction generally perpendicular to the axis of said handle; and an elongated guard connected to said handle, said guard extending along said handle substantially parallel to the axis of said handle, said guard terminating in a plate;

incising the skull of said mammal;

positioning said surgical instrument in a position wherein said grinding burr is below said scalp of said mammal but above said skull of said mammal and wherein said guard is below said skull of said mammal but above said dura of said mammal; and cutting said skull of said mammal with said burr to thereby remove said cranial bone.

13. A method according to claim 12, wherein said mammal is a human.

14. A method according to claim 12, wherein said plate includes an upturned tip, wherein said method further includes the step of separating said dura from said skull with said upturned tip.

15. A method according to claim 12, further comprising the step of separating said dura from said skull using an endoscope.

16. A surgical instrument comprising:

an elongated handle, said handle having an operator gripping end and an actuating end, said handle including an axial bore passing a drive shaft;

a cutting means extending from said handle at said actuating end in a direction generally perpendicular to the axis of said handle, said cutting means actuated by said drive shaft;

a collar securable to said handle and movable with respect thereto along at least a portion of said handle;

an elongate guard connected to said collar and extending along said handle in a direction generally parallel to the axis of said handle, said guard terminating in a flattened, broadened plate, said plate terminating in an upturned tip.

17. A surgical instrument according to claim 16, wherein said cutting means is a side-biting burr.

18. A surgical instrument comprising:

an elongated handle having an operator gripping portion and a head portion;

a grinding burr mounted to said handle at said head portion and rotatable about an axis generally perpendicular to the axis of said handle; and an elongated guard connected to said handle;

said head portion, said burr, and said guard being suitably dimensioned so that said burr may cut the skull of a human infant when said head portion is beneath the scalp of said human infant and said guard is beneath said skull of said human infant.

19. A surgical instrument according to claim 18, wherein said burr is a side-biting burr.

20. A surgical instrument comprising:

an elongated handle having an operator gripping portion, said handle including a grinding burr rotatably mounted to said handle opposite said operator gripping portion, said grinding burr having an axis of rotation; and an elongated guard connected to said handle, said guard extending along said handle, wherein substantially the entire length of said guard is substantially perpendicular to the axis of rotation of said grinding burr.

21. A surgical instrument comprising:

an elongated handle having an operator gripping portion, said handle including a grinding burr rotatably mounted to said handle opposite said operator gripping portion, said burr terminating in a tip, said grinding burr substantially perpendicular to said handle: and an elongated guard cantilevered to said handle, said guard terminating in a broadened, flattened portion spaced apart from said tip.

22. A method of cranial surgery for a mammal, the method comprising the steps of:

providing an endoscope, said endoscope including a proximal end grippable by a user and a distal end; said endoscope transmitting an image from said distal end to said proximal end;

positioning said endoscope between the inner table of the skull of said mammal and the dura of said mammal; and separating said dura from said skull using said distal end of said endoscope while observing the image transmitted by said endoscope, and continuing to dissect said dura from said skull.

* * * * *